United States Patent [19]

Ferretti et al.

[11] Patent Number: 4,764,469
[45] Date of Patent: Aug. 16, 1988

[54] STREPTOKINASE-CODING RECOMBINANT VECTORS

[75] Inventors: Joseph J. Ferretti; Horst Malke, both of Oklahoma City, Okla.

[73] Assignee: Board of Regents for the University of Oklahoma, Norman, Okla.

[21] Appl. No.: 585,417

[22] Filed: Mar. 2, 1984

[51] Int. Cl.$^4$ .......................... C12N 1/20; C12N 7/00; C12N 9/70; C12N 15/00; C07H 15/12; C12P 21/00; C12P 21/02

[52] U.S. Cl. .................................... 435/216; 435/68; 435/70; 435/172.3; 435/253; 435/320; 536/27; 935/14; 935/29

[58] Field of Search ................ 435/68, 70, 172.3, 317, 435/216, 243, 253; 935/29; 536/27

[56] References Cited

U.S. PATENT DOCUMENTS 4,532,211 7/1985 Sako et al. ........................ 435/172.3

OTHER PUBLICATIONS

Jackson et al., Biochemistry 21:6620–6625, 1982.
Jackson et al., In Methods in Erzymology, vol. 80: 387–394, 1981.

Primary Examiner—Thomas G. Wiseman
Assistant Examiner—Thomas D. Mays
Attorney, Agent, or Firm—Dunlap, Codding & Peterson

[57] ABSTRACT

A recombinant vector adapted for transformation of a suitable bacterial microorganism host to produce and secrete streptokinase. The recombinant vector comprises a plasmid into which a polydeoxyribonucleotide fragment from Streptococcus equisimilis H46A which codes for streptokinase synthesis and secretion has been inserted. The transformant bacterial microorganism including this recombinant plasmid vector produces streptokinase suitable for clinical fibrinolytic usage after purification.

40 Claims, 1 Drawing Sheet

STREPTOKINASE-CODING RECOMBINANT VECTORS

BACKGROUND OF THE INVENTION

A significant medical problem, namely thromboembolism, is presented by the occlusion of blood vessels due to the presence of thrombi (blood clots). Such thromboembolisms are potentially fatal, often affecting organs such as the heart or lungs. This blockage of normal blood circulation may lead to irreversible tissue damage as metabolizing cells are deprived of oxygen, nutrients and a path for disposal of waste products. A thromboembolic event, as described above may, for example, result from the formation of a blood clot in an arterioschlerotically altered artery. Such a clot may loosen and circulate to smaller arteries until it reaches an artery or arteriole too small to permit passage of the clot. The clot thereby blocks this small artery and prevents or inhibits the passage of blood therethrough.

The restoration of normal blood flow through such clot-blocked blood vessels, particularly in time to prevent tissue damage, is an important curative goal of modern medical practice. Another medical approach to the thromboembolytic problem is to prevent the formation of vascular blood clots when conditions known to result in such clot formations are known or suspected to exist.

Certain thrombolytic agents facilitate the in vivo lysis or dissolution of blood clots. One of these agents is the bacterial protein streptokinase.

Streptokinase, a protein produced and secreted by hemolytic streptococci, was discovered and shown to cause lysis of clots containing human fibrinogen by Tillett and Garner (J. Exp. Med. 58:485 [1933]). While the mechanism of such fibrinolysis is not totally understood, streptokinase itself is believed to bind and activate human plasminogen, the fibrinolytically inactive precursor of plasmin. The activation of such plasminogen results in the appearance of plasmin, a fibrinolytic enzyme which hydrolyzes clot fibrinogen (Castellino TIBS, p. 1 [January 1979]).

Streptokinase is a thrombolytic agent currently being used for the lysis of intravascular thrombi in pulmonary or peripheral blood vessels (Marder, Ann. Intern. Med. 90: 802 [1979]). Recent studies of intracoronary administration of streptokinase in the treatment of acute myocardial infarction patients indicate a beneficial effect on the early course of acute myocardial infarction (Khaja et al. N.E. J. Med. 308, p. 1305 [1983] and Anderson et al. N.E. J. Med. 308, p. 1312 [1983]).

Streptokinase from serological group C Streptococci has been purified for clinical usage and studied by several investigators. The primary source of this streptokinase has been the culture fluid resulting from the growth of the beta-hemolytic group C organism *Streptococcus equisimilis*. This culture fluid contains, in addition to streptokinase (a single-chain protein with a molecular weight of 45,000 to 50,000), a number of other extracellularly secreted substances. Since many of these other substances are toxic or potentially toxic to humans, the preparation of streptokinase from culture fluid for clinical usage involves multiple steps which must be performed with great care to ensure a clinically acceptable product.

The c-DNA sequences of mammalian urokinase and tissue-type plasminogen activator have been cloned previously (Pennica et al., Nature 301, p. 214 [1983] and Ratzkin et al., Proc. Nat. Acad. Sci. 78, p. 3313 [1981]).

A publication by Sako et al. (Mol. Gen. Genet. 190, p. 271 [1983]) describes the cloning of a staphylokinase-producing *Escherichia coli* transformant. A polydeoxynucleotide sequence sak coding for staphylokinase, which is a plasminogen activating protein having a size of about 15 kd, was excised from a native staphylococcal-residing bacteriophage (Pφ-2) and ligatively inserted into plasmid pBR322. This sak-modified plasmid was used to transform *Escherichia coli* K12 and the resultant staphylokinase-producing *Escherichia coli* transformant was found to secrete amounts of staphylokinase into a culture medium.

SUMMARY OF THE INVENTION

A recombinant vector adapted for transformation of a suitable host to produce streptokinase. The recombinant vector comprises a vector into which a polydeoxyribonucleotide fragment which codes for the synthesis and secretion of streptokinase has been inserted. The transformant microorganism including this recombinant vector synthesizes and secretes streptokinase. The transformant microorganism may be cultured in a suitable nutrient medium to produce a streptokinase-rich culture, from which streptokinase may be isolated.

DESCRIPTION OF THE PREFERRED EMBODIMENTS

Figure 1:
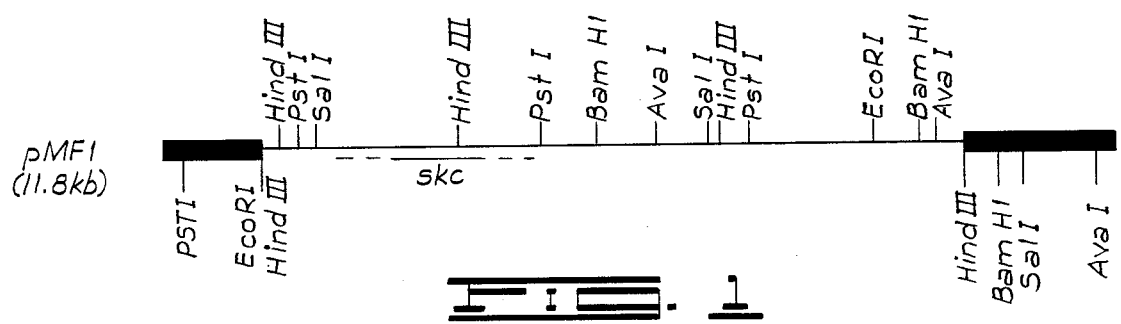
FIG. 1 is a restriction endonuclease map of plasmid pMF1.

In accordance with the present invention, a first vector is digested with a restriction endonuclease to produce linear first vector DNA. The first vector is preferably a plasmid, which is preferably obtained from a microbial source of the genera Escherichia, Saccharomyces, Streptococci, Bacillus, Neurospora, or Streptomyces. More preferably, the first vector is a plasmid obtained from a microbial source of the species *Escherichia coli*. Other suitable sources for the first vector include *Saccharomyces cerevisiae*, *Bacillus subtilus*, *Streptococcus sanguis*, *Streptococcus mutans*, and *Neurospora crassa*. Most preferably, the plasmid is the plasmid pBR322, which may be obtained from *Escherichia coli* RRl, NRRL B-12014, and which has been described by Bolivar et al. (Gene, 2, p. 95, [1977]). The restriction endonuclease for digesting the first vector is preferably either Pst I or Hind III.

The linear first vector DNA is ligated with a first polydeoxyribonucleotide fragment which codes for the synthesis and secretion of streptokinase, to produce a first recombinant vector comprising a first vector into which a polydeoxyribonucleotide fragment which codes for the synthesis and secretion of streptokinase has been inserted.

The first polydeoxyribonucleotide fragment coding for the synthesis and secretion of streptokinase is preferably obtained by digesting the chromosomal DNA of a streptokinase-producing microorganism with a restriction endonuclease, to produce at least one linear DNA fragment which codes for synthesis and secretion of streptokinase. While streptokinase appears to be exported from *Streptococcus equisimilis* and from pMF1-transformed *Escherichia coli* HB101, the mechanism of such extracellular export has not been completely defined. The terms 'secrete' and 'secretion,' as used in this specification and accompanying claims, are broadly meant to indicate an extracellular export of streptokinase. Preferably, the streptokinase-producing microorganism which is a source of the first polydeoxynucleotide fragment is a hemolytic microbe, and is more preferably of the genus Streptococcus, and is most preferably of the species *Streptococcus Equisimilis*. Most preferred is *Streptococcus equisimilis* strain H46A, serological group C. The restriction endonuclease with which the DNA of the streptokinase-producing microorganism is digested is preferably Sau 3A or Pst I.

The polydeoxyribonucleotide fragment which codes for the synthesis and secretion of streptokinase is ligated with linear DNA from a second vector, which preferably comprises a bacteriophage, and most preferably comprises lambda L47 bacteriophage. The linear second vector DNA is preferably formed by digesting the second vector DNA with at least one restriction endonuclease, preferably Bam H1. Ligation of the linear polydeoxyribonucleotide fragment which codes for synthesis and secretion of streptokinase with linear second vector DNA results in production of a second recombinant vector. The second recombinant vector is preferably infectively added to a suitable second host, which preferably comprises a microorganism, and more preferably comprises a bacterium. The bacterium preferably is of the genus Escherichia, and is more preferably of the species *Escherichia coli*. The bacterium most preferably comprises *Escherichia coli* strain WL95 (P2). Those infected second hosts which produce streptokinase are selected and cloned.

DNA from the second recombinant vectors of streptokinase-producing second hosts is preferably partially digested with a restriction endonuclease, which preferably is the same restriction endonuclease with which the first vector is digested as described above, and which preferably comprises Hind III or Pst I. The linear polydeoxyribonucleotide fragments produced by digestion of DNA from the streptokinase-producing second recombinant vectors comprise a preferred source of first polydeoxyribonucleotide fragments which code for the synthesis and secretion of streptokinase. As described above, a first polydeoxyribonucleotide fragment coding for synthesis and secretion of streptokinase is ligated with linear first vector DNA to produce a first recombinant vector.

FIG. 1 shows a restriction endonuclease map of the plasmid pMF1. This plasmid comprises a first recombinant vector which has been produced in accordance with the process just described, when the first vector is pBR322 and is digested by Hind III, when the streptokinase-producing microorganism is *Streptococcus equisimilis* strain H46A, serological group C and is digested with Sau 3A, when the second vector is lambda L47 bacteriophage and is digested with Bam H1, when the second host is *Escherichia coli* WL95 (P21) and when the second recombinant vector is digested with Hind III.

The first recombinant vector is infectively added to a suitable first host, which preferably comprises a microorganism, and more preferably comprises a bacterium. The bacterium is preferably of the genus Escherichia, and more preferably of the species *Escherichia coli*. Most preferred is the *Escherichia coli* strain HB101. This infective addition results in a streptokinase-producing transformed first host including a recombinant first vector which comprises a first vector into which a first polydeoxyribonucleotide fragment which codes for streptokinase synthesis and secretion has been inserted.

Infection of the *Escherichia coli* HB101 strain with the recombinant plasmid pMF1 as described above results in the transformed *Escherichia coli* strain HB101 (pMF1). Cultures of *Escherichia coli* HB101 (pMF1) have been deposited with the American Type Culture Collection, Rockville, Maryland, which deposit has been accorded Accession No. 39613.

The transformed first host, produced as described above, is cultured in a suitable nutrient medium to form a streptokinase-rich culture. Streptokinase thereafter may be isolated from this culture. After purification, this streptokinase is suitable for clinical fibrinolytic use.

EXAMPLE I

ISOLATION OF *STREPTOCOCCUS EQUISIMILIS* H46A CHROMOSOMAL DNA

*Streptococcus equisimilis* strain H46A (serological group C) was cultured overnight as a standing culture at 37° C. in 500 ml brain-heart infusion broth (Difco). The *Streptococcus equisimilis* cells were harvested by centrifugation and washed with cold TES buffer (0.03M Tris, pH 8.0; 0.005M EDTA; and 0.05M NaCl). The cells were resuspended in 15 ml of 25 weight percent glucose containing 0.03M EDTA and then mutanolysin (Dainippon Pharmaceutical Co., Osaka, Japan) dissolved in TES buffer was added to a concentration of about 2mg/ml and this cell suspension incubated at 37° C. for 30 minutes. At this point, 12.5 mg of the proteolytic enzyme Pronase, which had been predigested for 30 minutes at 37° C. as a TES solution of about 5 mg Pronase per ml, was added to the cell suspension and this resultant mixture subjected to an incubation at 37° C. for 30 minutes. After incubation the cells in the mixture were then subjected to further lysis by the addition of 10 ml of 2 weight percent sodium dodecyl sulfate in TES and 8.5 ml of 5M sodium perchlorate in TES to produce a lysate.

The lysate was then repeatedly extracted with a phenolchloroform (2:1) solution until no further protein appeared at the aqueous-organic interface. The DNA was then precipitated from the aqueous phase by the addition of two volumes of ethanol thereto. The DNA precipitate was washed with cold 70% ethanol, dissolved in TES buffer and purified further by centrifugation in a cesium chloride-ethidium bromide buoyant density gradient. Following dialysis against 10 mM Tris, pH 7.6 with 1 mM EDTA to remove cesium chloride and ethidium bromide, the H46A DNA, having an average size of about 50 kb, was stored at 4° C.

EXAMPLE II

CLONING OF *STREPTOCOCCUS EQUISIMILIS* H46A DNA INTO BACTERIOPHAGE LAMBDA L47

The procedure of Cameron et al. (Nucl. Acids Res. 4, p. 1429 [1977]) was utilized to prepare DNA from Amersham-supplied bacteriophage lambda L47 (Loenen et al., Gene 20, p. 249 [1980]) obtained from high titer bacterial lysates (i.e. containing at least $10^{10}$ PFU/ml) after precipitation of protein by sodium dodecyl sulfate-potassium sulfate additions. The bacteriophage lambda L47 DNA was digested completely with the restriction endonuclease Bam H1 to form digested bacteriophage lambda L47 DNA fragments.

The *Streptococcus equisimilis* H46A DNA, prepared as described above in Example I, was digested with the restriction endonuclease Sau 3A according to the procedure of Maniatas et al. (*Molecular Cloning: A Laboratory Manual*, Cold Spring Harbor Laboratory, Cold Spring Harbor, N.Y. [1982]) to produce a mixture of H46A DNA fragments. The mixture of H46A DNA fragments was layered on a 37 ml, 10% to 40% linear sucrose density gradient containing 1 mM NaCl, 20 mM Tris (pH 8.0) and 5 mM EDTA and then subjected to centrifugation at 25,000 rpm for 21 hours in a SW27 Beckman ultracentrifuge rotor. Fractions having volumes of 1 ml were collected from the centrifuged gradient and the size distribution of DNA fragments in each fraction was determined by electrophoresis thereof in a 0.5% agarose (Sigma) gel and comparisons of the fragment migrations with those of reference bacteriophage lambda DNA fragments having known sizes. The fractions having *Streptococcus equisimilis* H46A DNA fragments sized from about 4 kb to about 15 kb were pooled, dialyzed against 10 mM Tris, pH 7.4 with 1 mM EDTA and then precipitated with cold ethanol. The precipitated DNA fragments were dissolved in 10 mM Tris, pH 7.4 with 1 mM EDTA at a concentration of 1 mg DNA per ml.

Ligation of the *Streptococcus equisimilis* H46A DNA fragments with the digested bacteriophage lambda L47 DNA was accomplished by combining, in a 10 µl volume, 1 µg of the pooled sized H46A DNA fragments; 1 µg of digested lambda L47 DNA, T4 DNA ligase and ligase buffer, according to the directions supplied with the Amersham lambda DNA in vitro packaging kit. Following a 12 hour incubation at 12° C., 4 µl of the now-ligated DNA mixture was packaged into lambda phage heads according to the conditions prescribed by the Amersham instructions referred to above.

A portion of the ligated phage thus produced was infectively added to each of two *Escherichia coli* lawns. One lawn contained strain WL95 (P2), which allows propagation only of recombinant clones containing DNA inserts and is not susceptible to phage P2-mediated interference (Loenen et al. Gene 20, p. 249 [1980]). The other lawn contained strain WL87, which allows propagation of recombinant clones as well as of reconstituted wild type lambda L47 phage.

The total packaging efficiency calculated from the WL87 lawn was $10^5$ PFU per p.4' µg of lambda L47 DNA and these recombinant clones (obtained from the WL95 (P2) lawn) represented a library of the *Streptococcus equisimilis* strain H46A chromosome.

EXAMPLE III

DETECTION OF RECOMBINANT PHAGES PRODUCING STREPTOKINASE

Activated plasminogen generates a caseinolytic as well as a fibrinolytic activity. The *Escherichia coli* which were treated with recombinant phage as described in Example II were cultured as plaques on plates of nutrient agar. These plates were then overlaid with a solution containing 50 mM Tris, pH 8.1, 150 mM NaCl, 10 µg/ml human plasminogen, 10 mg agar/ml and 10 volume percent skim milk and were then incubated at 37° C. for at least 2 hours. The presence of streptokinase in a plaque resulted in the formation of a surrounding clear zone in the overlaying gelled solution, indicative of casein hydrolysis by activated plasminogen. Of the more than 8,000 plaques thus studied, 10 were found which produced surrounding clear zones of caseinolysis. These ten recombinant streptokinase-producing clones were designated as lambda L47 (A to K) skc, isolated and stored for further study.

EXAMPLE IV

PHYSICAL MAPPING OF RECOMBINANT LAMBDA L47 skc CLONES

The ten recombinant streptokinase-producing lambda clones described above were isolated from high-titer lysates ($10^{10}$ PFU/ml) according to the procedures described by Davis et al. (*A Manual for Genetic Engineering: Advanced Bacterial Genetics*, Cold Spring Harbor Laboratory, Cold Spring Harbor, N.Y. [1980]). Restriction endonuclease digestion of the DNA from these clones was performed using the restriction endonucleases Bam H1, Eco R1 and Hind III, again according to procedures described in Davis et al. The DNA digests thus obtained, together with DNA markers of known molecular sizes, were subjected to electrophoresis in 1% agarose gels. The resultant gel distribution of DNA fragments from the streptokinase-producing lambda clones indicated that the size of the *Streptococcus equisimilis* H46A DNA fragments inserted in these clones ranged from 7 kb to 15 kb. A 1.9 kb Hind III fragment was common to all ten clones which suggested that this 1.9 kb fragment specified at least a part of the skc (streptokinase) gene. The patterns from lambda L47E skc and lambda L47G skc were identical.

EXAMPLE V

SUBCLONING OF THE skc GENE INTO *ESCHERICHIA COLI* PLASMID VECTORS

The DNA from lambda L47E skc was partially digested with the restriction endonuclease Hind III and then combined with the DNA of plasmid pBR322 which had been completely digested with the same restriction endonuclease. A ligation mixture comprising the above described digested DNA fragments, T4 DNA ligase and ligase buffer was incubated at 12° C. for 12 hours to ligate the digested plasmid pBR322 DNA with the partially digested DNA from lambda L47E skc. The ligation products were used to transform *Escherichia coli* strain HB101 (a commonly used strain K-12 subspecies) by following the procedure described by Dagert et al. (Gene 6, p. 23, [1979]), to produce the transformed microorganism *Escherichia coli* HB101 (pMF1).

The preparation of transformed *Escherichia coli* strain HB101 cells was plated on LB agar plates (Lennox, Virology 1, p. 190 [1955]) which contained 50 µg ampicillin/ml and 260 ampicillin restraint (Ap$^r$) clones were obtained. When these Ap$^r$ clones were tested for growth on LB agar plates containing 12.5 µg tetracycline/ml, 37 Tc$^s$ colonies were found. When the Tc$^s$ colonies were tested for caseinolytic activity (as described in Example III) one colony was found to yield the surrounding clear zone characteristic of streptokinase production.

The plasmid obtained from this streptokinase-producing transformant was isolated by buoyant density gradient ultracentrifugation and designated plasmid pMF1. Six restriction endonucleases (Hind III, Pst I, Sal I, Bam H1, Ava I and Exo RI) were utilized to digest plasmid pMF1 by the digestion procedure described in Example IV. With the data resulting from these digestions a map of the restriction sites was determined and is shown in FIG. 1. Plasmid pMF1 was found to have a molecular size of about 11.8 kb and contained a 7.4 kb insert in its Hind III site which included the skc gene. Partial Hind III digests of the original lambda L47E skc DNA also contained 7.4 kb fragments. Plasmid pMF1 and DNA in the lambda L47E skc clone both also contained four Hind III fragments of size 2.65, 2.60, 1.9 and 0.2 kb. These identical fragments confirmed that the skc-related sequences of the lambda L47E skc DNA and the plasmid pMF1 DNA were identical, and that the skc-related sequences of plasmid pMF1 were derived from the skc-related sequences of lambda L47E.

EXAMPLE VI

CONFIRMATION THAT THE CLONED skc GENE ORIGINATED IN *STREPTOCOCCUS EQUISIMILIS* STRAIN H46A To confirm that the cloned skc gene was that of *Streptococcus equisimilis* strain H46A, the hybridization procedure described by Southern (J. Mol. Biol. 98, p. 503 [1975]) was utilized.

Plasmid pMF1 having a polydeoxynucleotide insert coding for streptokinase and a size of about 7.4 kb was subjected to digestion with the restriction endonuclease Pst I and the four resultant pMF1 fragments having sizes of 6.0, 2.5, 2.2 and 1.1 kb were separated by electrophoresis in 0.8% low temperature melting agarose. The 2.5 kb Pst I fragment, when subcloned into plasmid pBR322, produced biologically active streptokinase and, therefore contained most, if not all, of the SKC structural gene. The 2.5 kb Pst I-produced pMF1 fragment was separated from other fragments and removed from the agarose by electroelution. This purified 2.5 kb fragment was precipitated from solution by the addition of ethanol and then dissolved in 10 mM Tris, pH 7.4 containing 1 mM EDTA. The dissolved fragment was nick translated according to the procedure described by Maniatas et al. (*Molecular Cloning: A Laboratory Manual*, Cold Spring Harbor Laboratory, Cold Spring Harbor, N.Y. [1982]) to form a $^{32}$P-labelled 2.5 kb fragment probe. Chromosomal DNA from *Streptococcus equisimilis* H46A and from *Escherichia coli* were immobilized on separate nitrocellulose filters. The $^{32}$P-labelled fragment probe was radioautographically found to hybridize only with immobilized DNA from *Streptococcus equisimilis* strain H46A, thus confirming that the 2.5 kb Pst I-produced pMF1 fragment originated in the *Streptococcus equisimilis* strain H46A.

EXAMPLE VII

IDENTIFICATION OF THE skc GENE PRODUCT

The caseinolysis reactivity used throughout the above described procedures to monitor the skc gene product as dependent on the presence of human plasminogen, indicating that the proteolytic skc gene product was dependent upon the human plasminogen and that no independent proteolytic activity was involved. This skc-related caseinolysis reactivity did not occur when bovine plasminogen was substituted for human plasminogen in the caseinolytic assay overlay. Streptococcal streptokinase is inactive for bovine plasminogen activation.

When diisopropylfluorophosphate, an irreversible inhibitor of serine-containing proteases, was included in the caseinolytic reaction system, there was not inhibition of caseinolysis. Streptokinase, not a serine-containing protease, is similarly unaffected by diisopropylfluorophosphate.

In an Ouchterlony immunodiffusion system, antibody specific to streptokinase was placed in a center well and purified streptokinase and supernatant from a transformant *Escherichia coli* strain HB101 (pMF1) culture were placed in separate surrounding wells. After diffusion through the gel an immunoprecipitate line of identity formed, indicating that streptokinase and the immunologically active component from the *Escherichia coli* strain HB101 (pMF1) culture were identical.

EXAMPLE VIII

EXPORT OF THE skc GENE PRODUCT BY *ESCHERICHIA COLI* TRANSFORMANTS

Supernatant culture fluids from the pMF1-containing transformant of *Escherichia coli* strain HB101 had levels of streptokinase activity consistent with secretion of the streptokinase from the *Escherichia coli* cells. Likewise, the overlaid caseinolysis assays of transformed bacteria colonies resulted in areas of casein hydrolysis having large diameters consistent with extracellular streptokinase production.

Cultures of the pMF1-transformed *Escherichia coli* strain HB101 were centrifugally separated when in the early stationary growth phase to produce a supernatant fluid and cell pellet. The pelleted cells were washed and treated by the osmotic shock procedure of Hazelbauer et al. (Cell. 16, p. 617 [1979]) to obtain periplasmic fluid and protein. Cytoplasmic cell proteins were obtained by the sonification of these osmotically shocked cells. When streptokinase activity was determined it was found that the supernatant fluid contained 17%; the periplasm, 30%; and the cytoplasm, 52% of the total activity. When this experiment was repeated, but with pMF1-transformed *Escherichia coli* HB101 cells which had been cultured in the stationary phase for at least 8 hours, the supernatant fluid contained the majority of the streptokinase activity, while the periplasm contained an indetectably low amount and the cytoplasm contained the residue.

With *Streptococcus equisimilis* H46A streptokinase appears to be a secreted protein. This may indicate, according to the signal hypothesis (Emr et al., J. Cell. Biol. [1980], 86, p. 701; Talmadge et al., Proc. Nat'l. Acad. Sci. [1980], 77, p. 3369; Gray et al., J. Bacteriol. [1981], 145, p. 422 and Roggerkamp et al., Proc. Nat'l. Acad. Sci. [1981], 78, p. 4466), that a precursor comprising streptokinase with an amino-terminal signal peptide is synthesized by *Streptococcus equisimilis* H46A (Michaelis et al., Ann. Rev. Microbiol. [1982], 36, p. 435; and Jackson et al., Biochem. [1982], 21, p. 6620). The pMF1-transformed *Escherichia coli* HB101 also appears to secrete streptokinase, which may indicate a commonality of secretion in gram-positive *Streptococcus equisimilis* H46A and gram-negative (pMF1) *Escherichia coli* HB101. The polydeoxynucleotide fragment from *Streptococcus equisimilis* contained in the pMF1 plasmid thus may code for streptokinase as well as for an amino-terminal signal peptide which is bound to streptokinase and which is hydrolyzed during a streptokinase secretion event.

Changes may be made in the sequence, operation and arrangement of the various elements, steps and procedures described herein without departing from the spirit and scope of the invention as defined in the following claims.

What is claimed is:

1. A recombinant vector adapted for transformation of a suitable bacterial host to produce streptokinase, said recombinant vector comprising a vector into which a polydeoxyribonucleotide fragment which codes for capable of operating to cause the synthesis and secretion of streptokinase has been inserted.

2. The recombinant vector of claim 1 wherein the vector is a plasmid obtained from a microbial source of the genus Escherichia.

3. The recombinant vector of claim 2 wherein the microbial source of the genus Escherichia is of the species *Escherichia coli*.

4. The recombinant vector of claim 3 wherein the vector is plasmid pBR322.

5. The recombinant vector of claim 1 wherein the polydeoxyribonucleotide fragment which codes for capable of operating to cause the synthesis and secretion of streptokinase is obtained from a microorganism of the genus Streptococcus.

6. The recombinant vector of claim 5 wherein the microorganism is of the species *Streptococcus equisimilis*.

7. The recombinant vector of claim 6 wherein the microbe is *Streptococcus equisimilis* strain H46A.

8. Recombinant plasmid pMF1 having the restriction endonuclease sites as shown by the restriction endonuclease map in FIG. 1 of the drawings.

9. A process for preparing a recombinant vector comprising a vector into which a polydeoxyribonucleotide fragment which codes for capable of operating to cause the synthesis and secretion of streptokinase has been inserted, comprising:
digesting a vector with a restriction endonuclease to produce linear vector DNA;
ligating the linear vector DNA with a polydeoxyribonucleotide fragment which codes for and is capable of operating to cause the synthesis and secretion of streptokinase, to produce a recombinant vector comprising a vector into which a polydeoxyribonucleotide fragment which codes for capable of operating to cause the synthesis and secretion of streptokinase has been inserted.

10. The process of claim 9 in which the polydeoxyribonucleotide fragment is prepared by digesting the chromosomal DNA of a streptokinase-producing microorganism with the same restriction endonuclease used to digest the vector, to produce a polydeoxyribonucleotide fragment which codes for capable of operating to cause the synthesis and secretion of streptokinase.

11. The process of claim 9 in which the restriction endonuclease is Pst I.

12. The process of claim 10 in which the restriction endonuclease is Pst I.

13. The process of claim 9 wherein the vector is a plasmid obtained from a microbial source of the genus Escherichia.

14. The process of claim 13 wherein the microbial source of the genus Escherichia is of the species *Escherichia coli*.

15. The recombinant vector of claim 14 wherein the vector is plasmid pBR322.

16. The process of claim 9 wherein the polydeoxyribonucleotide fragment which codes for capable of operating to cause the synthesis and secretion of streptokinase is obtained from a microorganism of the genus Streptococcus.

17. The process of claim 16 wherein the microorganism is of the species *Streptococcus equisimilis*.

18. The process of claim 17 wherein the microorganism is *Streptococcus equisimilis* strain H46A.

19. A transformant bacterial microorganism which contains a recombinant vector, comprising a vector into which a polydeoxyribonucleotide fragment which codes for capable of operating to cause the synthesis and secretion of streptokinase has been inserted.

20. The transformant microorganism of claim 19 which is of the genus Escherichia.

21. The transformant microorganism of claim 20 which is of the species *Escherichia coli*.

22. The transformant microorganism of claim 21 which is *Escherichia coli* strain HB101.

23. The transformant microorganism of claim 19 wherein the vector is the plasmid pBR322.

24. The transformant microorganism of claim 19 wherein the recombinant vector is plasmid pMF1.

25. *Escherichia coli* HB101 (pMF1).

26. A process for preparing a streptokinase-producing microorganism which comprises transforming into a suitable bacterial microorganism host a recombinant vector comprising a rector into which a polydeoxyribonucleotide fragment which codes for capable of operating to cause the synthesis and secretion of streptokinase has been inserted.

27. The process of claim 26 in which the microorganism host is of the genus Escherichia.

28. The process of claim 27 in which the microorganism host is of the species *Escherichia coli*.

29. The process of claim 28 in which the microorganism host is *Escherichia coli* HB101.

30. The process of claim 26 in which the recombinant vector is pMF1.

31. A polydeoxyribonucleotide fragment isolated from any genome which codes for and is capable of operating to cause the synthesis and secretion of streptokinase.

32. The polydeoxyeribonucleotide fragment of claim 31 which has restriction endonuclease cleavage sites at the termini thereof.

33. The polydeoxyribonucleotide fragment of claim 32 which has about 7400 deoxyribonucleotide base pairs.

34. The polydeoxyribonucleotide fragment of claim 32 in which the cleavage sites are for the restriction endonuclease Pst I.

35. The polydeoxyribonucleotide fragment of claim 31 which is obtained from a microorganism of the genus Streptococcus.

36. The polydeoxyribonucleotide fragment of claim 35 wherein the microorganism is *Streptococcus equisimilis* strain H46A.

37. A process for producing streptokinase comprising:
culturing a transformant bacterial microorganism, which includes a recombinant vector comprising a vector into which a polydeoxyribonucleotide fragment which codes for capable of operating to cause the synthesis and secretion of streptokinase has been inserted, in a suitable nutrient medium to form streptokinase; and
isolating streptokinase from said culture.

38. The process of claim 37 wherein the transformant microorganism is of the species *Escherichia coli*.

39. The process of claim 38 in which the transformant microorganism is *Escherichia coli* HB101 (pMF1).

40. The process of claim 9, wherein the process further comprises isolating said vector.

* * * * *